United States Patent
Pennington et al.

Patent Number: 5,117,011
Date of Patent: May 26, 1992

[54] NON-CATALYTIC OXIDATION OF PROPYLENE TO PROPYLENE OXIDE

[75] Inventors: Ruford T. Pennington, Sulfur; Michael C. Fullington, Lake Charles, both of La.

[73] Assignee: Olin Corporation, Cheshire, Conn.

[21] Appl. No.: 741,377

[22] Filed: Aug. 7, 1991

[51] Int. Cl.$^5$ .................. C07D 301/04; C07D 303/04
[52] U.S. Cl. ........................................ 549/523
[58] Field of Search ......................... 599/523

[56] References Cited

U.S. PATENT DOCUMENTS

| | | | |
|---|---|---|---|
| 1,911,746 | 3/1933 | Burke et al. | 549/523 |
| 1,995,991 | 3/1935 | Lenher | 260/156.5 |
| 2,392,316 | 1/1946 | Dreyfus | 260/573 |
| 2,530,509 | 11/1950 | Cook | 260/348.5 |
| 2,689,253 | 9/1954 | Robertson et al. | 260/541 |
| 3,026,333 | 3/1962 | Wegner et al. | 260/348.5 |
| 3,132,156 | 5/1964 | Lemon et al. | 260/348 |
| 3,483,229 | 12/1969 | Bernard | 260/348.5 |
| 4,785,123 | 11/1988 | Pennington | 549/532 |
| 4,943,643 | 7/1990 | Pennington et al. | 549/532 |

FOREIGN PATENT DOCUMENTS

| | | | |
|---|---|---|---|
| 986127 | 3/1976 | Canada | 549/523 |
| 861373 | 2/1961 | United Kingdom | 549/523 |
| 960332 | 6/1964 | United Kingdom | . |

*Primary Examiner*—J. E. Evans
*Attorney, Agent, or Firm*—Gregory S. Rosenblatt; Paul Weinstein

[57] ABSTRACT

There is provided a process for the non-catalytic oxidation of gaseous hydrocarbons, preferably propylene. A mixture of propylene, oxygen and a inert diluent are provided to a rector vessel capable of maintaining an isothermal reaction. Maintaining a temperature in the range of about 200° C. to about 350° C. and a propylene partial pressure of about 80 psia to about 300 psia provides the highest propylene oxide selectivity.

25 Claims, 3 Drawing Sheets

NON-CATALYTIC OXIDATION OF PROPYLENE TO PROPYLENE OXIDE

BACKGROUND OF THE INVENTION

This invention relates to a process for the direct oxidation of alkylenes and alkylene derivatives. In particular, propylene is directly oxidized to propylene oxide in an isothermal reaction which does not require the presence of a catalyst.

Alkylene oxides (vicinal epoxy alkanes), and particularly propylene oxide, are widely used chemicals. The alkylene oxides have been polymerized with a wide variety of monomers to yield polymers which are useful in coating compositions and in the manufacture of molded articles such as urethane foams. They are also reacted with alcohols to yield monoalkyl ethers which have utility as solvents in many commercial processes and which are useful as components for synthetic turbojet lubricants.

Many methods to produce propylene oxide are known throughout the art. One method, referred to as the chlorohydrin process, involves the reaction of chlorine and water to form hypochlorous acid which is then reacted with propylene forming propylene chlorohydrin. The propylene chlorohydrin is then dehalogenated to yield propylene oxide.

U.S. Pat. Nos. 4,785,123 and 4,943,643 to Pennington, assigned to a common assignee, and incorporated herein by reference disclose vapor phase oxidation of olefins by bubbling the gases through a molten nitrate salt catalyst. The salts are a mixture of potassium and sodium salts containing 20-80 wt. % sodium nitrate. Besides a catalyst, the molten salts serve as an isothermal medium for any co-catalyst and absorb large the quantities of heat generated during the exothermic oxidation reaction.

Non-catalytic oxidation reactions have also been disclosed. Co-pending U.S. patent application Ser. No. 07/620,675 by Fullington, filed Dec. 3, 1990, assigned to a common assignee and is incorporated herein by reference discloses the direct oxidation of propylene with an oxygen. The operating temperature is from 100° C. to 300° C. at a pressure above 300 psia (pounds per square inch absolute).

U.S. Pat. No. 2,530,509 by Cook discloses reacting propane and propylene with oxygen in a plug flow reactor having a large surface area relative to the volume occupied by the reacting gases. The large surface area is required to remove heat generated during the oxidation reaction. While the direction of gas flow may be reversed, there is no suggestion of circulating the gases to obtain an isothermal reaction zone.

U.S. Pat. No. 3,132,156 to Lemon et al. discloses a reaction vessel for the oxidation of propylene which provides substantial homogeneity of reactants and essentially isothermal conditions throughout the reaction zone. The reaction temperature is maintained within the range of 425° C. to 575° C.

Non-catalytic direct oxidation has advantages over catalyzed oxidation or processes requiring intermediate reaction steps. There are fewer process steps to monitor and fewer chemical components to maintain, both of which reduce cost. However, until now, non-catalytic direct oxidation has been limited by low yield and poor propylene oxide selectivity. Propylene oxide selectivity is the molar percentage of propylene oxide produced for every mole of propylene which reacts within the reactor vessel.

SUMMARY OF THE INVENTION

Accordingly, it is an object of the present invention to provide a process for the non-catalytic oxidation of alkylenes, such as propylene, which has a higher yield than prior art processes. It is a feature of the invention that by maintaining the reaction, temperature, pressure and time within critical operating parameters both high propylene oxide yields and selectivity are obtained. Yet another feature of the invention is that the flow of gases within the reaction vessel provide an essentially isothermal reaction. In a preferred embodiment, carbon dioxide is present as a diluent.

One advantage of the invention is that the reaction does not require the presence of a catalyst. In the case of the production of propylene oxide by this process, the molar percent of reacted propylene converted to propylene oxide has been measured to be in excess of 40%. Yields in excess of 50% are believed obtainable with the process.

Accordingly, there is provided a process for the production of an alkylene oxide or mixture of alkylene oxides. A gaseous mixture containing at least one hydrocarbon selected form the group consisting of alkylenes, alkanes and derivatives thereof and oxygen are circulated in a reaction vessel. The hydrocarbon is oxidized under essentially non-catalytic, substantially isothermal conditions while the partial pressure of the hydrocarbon is maintained at from about 80 to about 300 psia and the reaction temperature is maintained at from about 200° C. to about 350° C.

The above stated objects, features and advantages as well as others will become more apparent from the specification and drawings which follow.

IN THE DRAWINGS

DESCRIPTION OF THE INVENTION

Figure 1:
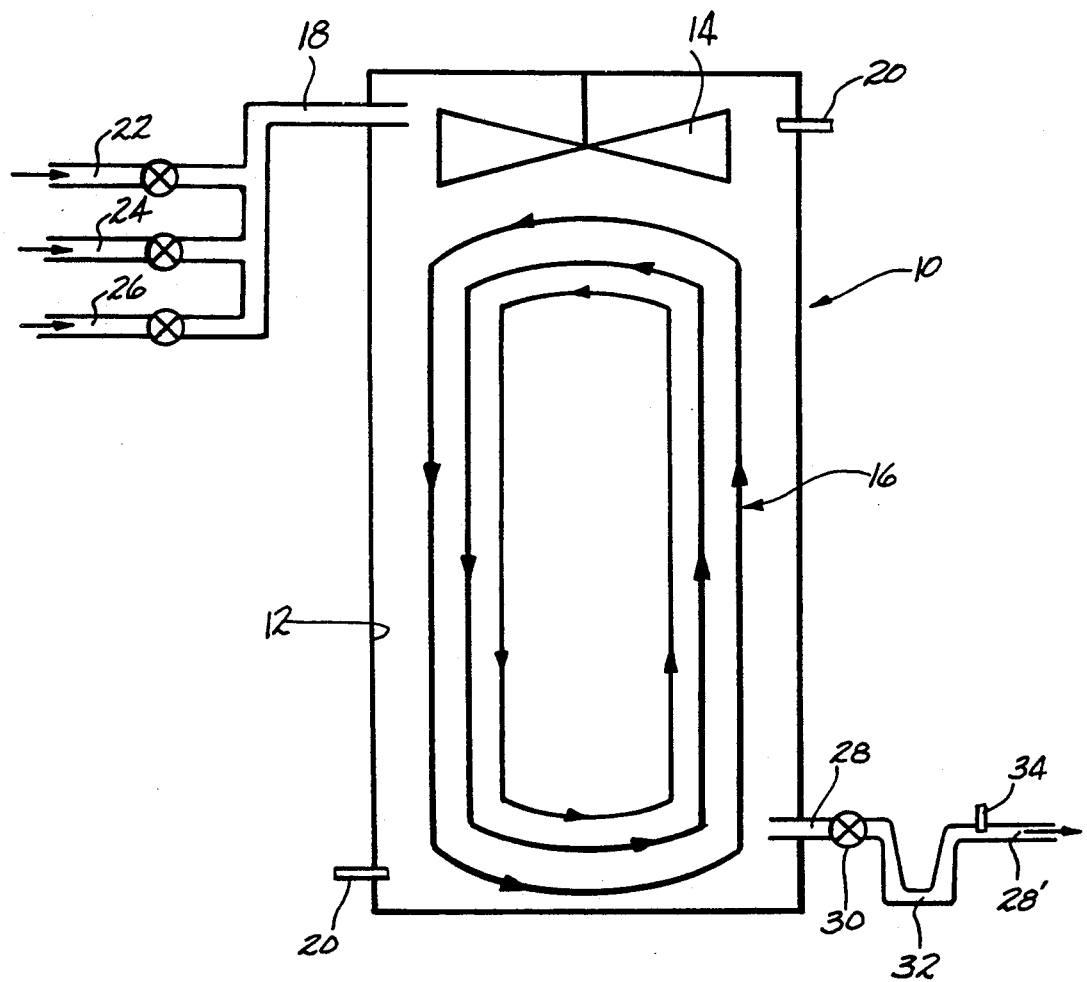
FIG. 1 shows in schematic a continuous stirred tank reactor used to circulate the mixture of gases in accordance with a first embodiment of the invention.

The hydrocarbons useful as reaction gases to be oxidized by the process of the invention can be broadly defined as alkylenes, alkanes and derivatives thereof generally having from 3 to 22 carbon atoms. This definition is intended to include terminal olefins selected from the group consisting of monofunctional and difunctional olefins having the following structural formulas, respectively:

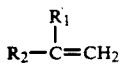

where $R_1$ is hydrogen or an alkyl chain, straight or branched, having 1 to 20 carbon atoms and $R_2$ is an alkyl chain, straight or branched, having 1 to 20 carbon atoms; and:

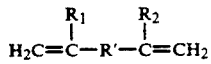

wherein $R_1$ and $R_2$ are hydrogen atoms or alkyl chains having 1 to 10 carbon atoms and $R'$ is from 2 to 10 methylene groups. The definition also includes cyclic olefins and internal olefins. The ring portions of the cyclic olefins can have up to 10 carbon atoms and one unsaturated bond and can be substituted with one or two alkyl radicals having 1 to 10 carbon atoms. The cyclic olefins are typically represented by the following structural formula:

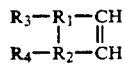

wherein $R_1$ and $R_2$ are alkylene radicals having 1 to 4 carbon atoms and $R_3$ and $R_4$ represent hydrogen atoms, or one or two alkyl radicals, straight or branched chain, having 1 to 10 carbon atoms. The internal olefins are represented by the following structural formula:

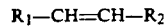

wherein $R_1$ and $R_2$ are straight chain or branched chain alkyl radicals having 1 to 10 carbon atoms.

The alkanes, alkylenes, derivatives and mixtures thereof useful as gaseous reactants in the process of the invention generally have up to, but do not exceed, about 22 carbon atoms per molecule, preferably not more than 12 carbon atoms per molecule. When a straight chain molecule is employed, it is preferred that such molecule not have more than five carbon atoms. When a cyclic compound is used, it is preferred that the cyclic compound not have more than 12 carbon atoms per molecule. Illustrative reactants include propane, propylene, isobutane, butane, cyclohexene and mixtures thereof. A preferred reactant within this group is propylene or a mixture of propylene and propane based on their commercial availability.

Representative other alkylene compounds or olefins are butene-1, butene-2, isobutylene, pentene-, hexene-1, pentene-2, cyclopentene, and cyclooctene. Other representative olefins are 2-methylbutene-1, 3-methylbutene-1, heptene-1, octene-1, hexene-2, hexene-3, octene-2, heptene-3, pentadecene-1, octadecene-1, dodecene-2, 2-methyl pentene-2, tetramethylethylene, methylethylethylene, cyclobutene, cycloheptene, 2-methylheptene-1, 2,4,4, -trimethylpentene-1,2-methylbutene-2, 4-methylpentene-2, and 2-ethyl-3-methylbutene-1.

Oxygen can be provided either as the pure gas or in a mixture with other gases. One such mixture is air which is preferred based on ready availability. Pure oxygen will be preferred in a commercial setting to minimize contamination from trace constitutents.

In addition to the gaseous hydrocarbon and the oxygen, a diluent is preferably present. When propylene is provided at high partial pressure and in high concentration, thermal cracking may break apart the carbon chains. The diluent reduces the concentration of propylene to eliminate or minimize thermal cracking. Among the suitable diluents are inert gases such as nitrogen and argon or mixtures of oxidation by-product gases such as acetaldehyde, methane and carbon dioxide. Diluents having high thermal capacity and thermal conductivity are preferred to assist in the circulation of heat. The most preferred diluent is carbon dioxide generated as a by-product of the oxidation reaction.

The gas feed stock is preferably provided in a concentration of from about 30 to about 85 volume percent (vol. %) propylene, from about 1 to about 20 vol. % oxygen and the balance $CO_2$ or other diluent. If air is the oxidant source, the ratio of oxygen to nitrogen in the air is considered in determining the feed stock ratio. More preferably, the propylene concentration is from about 40 to about 75 vol. %, the oxygen from about 2 to about 17 vol. % and the balance $CO_2$. Most preferably, the concentration of oxygen is from about 5 to about 15 vol. %.

The oxygen concentration is critical to the noncatalytic oxidation. The oxygen concentration influences the rate of the exothermic reaction. When a steady state reaction is achieved, the inflow of oxygen generates heat at a rate sufficient to balance the heat lost by conduction and as heated offgas. Preferably, from about 0.5 vol. % to about 3 vol. % $O_2$ remains unreacted and recovered as residual oxygen.

FIG. 1 illustrates in schematic a continuous stirred tank reactor 10 to oxidize propylene. The reactor 10 is formed from a material inert to the reaction gases at the operating temperatures and pressures such as 304 stainless steel. The interior walls 12 of the reactor are preferably oxide free. Carbon particles have been detected adhering to oxidized reactor surfaces while no such particles have been detected when the reactor walls are oxide free.

An agitator 14, which may be any device capable of generating a vortex 16 of circulating gases extending the length of the reactor 10, is located within the reactor in close proximity to the feed stream 18 of reaction gases. Suitable agitators include mechanical propellers and rotating wheels having fins for air agitation. Magnetic stirring as well as other means of achieving a vortex are satisfactory.

To demonstrate the criticality of circulating the reaction gases, two thermocouples 20 were mounted in the walls of the reactor 10 extending into the reaction chamber. With agitation, the temperature difference between thermocouples was on the order of about 1-4 degrees centigrade. Without agitation, the temperature difference was up to 50° C. For the purpose of this application, "substantially isothermal" means a preferred temperature gradient of less than about 5° C. within the reactor vessel.

Feed gas streams, propylene 22, oxygen 24 and carbon dioxide 26 are mixed in a desired ratio and introduced to the reactor 10. Preferably, the feed gas 18 is preheated to a temperature of at least 100° C. just prior to introduction into the reaction vessel. One exemplary means of preheating the feed gas is by steam tracing. Preheating the gas accelerates initiation of the oxidation reaction. Little propylene oxide was detected when the reactor temperature was below 195° C.

The offgas 28 is removed from the base of the reactor. A back pressure regulator 30 controls the pressure inside the reactor 10. Other methods of controlling the reactor pressure such as check valves or electronic means may also be used. The offgas 28 is passed through a cold trap to condense propylene derivatives. The cold trap is maintained at about 0° C. by immersion in an ice water bath. Other means to trap reaction product are also suitable. For example, water at a PH of from about 7.0 to 7.5 will absorb the product.

After exiting the cold trap 32, the offgas 28' is collected in a suitable gas containment structure. A sensor 34 interconnected to a gas chromatograph can be used to evaluate the product and determine the conversion rate of propylene to propylene oxide.

For optimum yields, the temperature of the reaction gases during oxidation is in the range of from about 200° C. to about 350° C. A more preferred range is from about 235° C. to about 300° C. while most preferred is from about 245° C. to about 290° C. Temperatures lower than about 200° C. are less preferred because the reaction rate is decreased and there is unexpectedly poor propylene oxide selectivity. Temperatures above about 325° C. are less preferred because combustion to $CO_2$ and coking occur.

The partial pressure of propylene in the reactor affects yield. While it had been expected that increasing the partial pressure would increase the yield in an approximately linear fashion, it has been determined that a critical pressure of about 200 psia optimizes the conversion to propylene oxide. A partial pressure of about 200 psia results in 50% selectivity of propylene oxide. A pressure of 300 psia seldom exceeds 40% selectivity. The partial pressure is calculated by multiplying the total pressure (absolute) and the volume percent of propylene as determined by analytical means.

The preferred propylene oxide partial pressure is from about 80 to about 300 psia. A more preferred partial pressure is from about 100 to about 250 psia, while a most preferred range is from about 120 to about 220 psia.

The residence time of the gases in the reactor influences propylene oxide selectivity. As the time increases, the selectivity for propylene oxide and its derivatives decrease. It is therefore desirable to minimize residence time. Residence times of less than about 150 seconds are preferred. More preferred is from about 5 to about 125 seconds and most preferred is from about 10 to about 100 seconds.

The advantages of the non-catalytic direct oxidation process will become more apparent from the Example which follows. The Example is intended to be exemplary and not to impose limitation on the utility of the invention. Except where indicated to the contrary, pressure is given in psia, temperature in degrees centigrade and time in seconds.

EXAMPLE

A 304 stainless steel continuous stirred tank reactor essentially as illustrated in FIG. 1 was employed. The reaction chamber was 3.5 inches in diameter by 13 inches deep. The interior surfaces were made oxide free by sand blasting followed by a deionized water rinse and drying. An agitator consisting of a rotating disk having perpendicularly extending fins was mounted to a top interior surface of the reactor.

The reaction gases (40–75 vol. % propylene, 6.5–9.3 vol. % oxygen and the balance nitrogen) were mixed and preheated to 100° C.–120° C. by steam tracing prior to introduction to the reactor. The offgas was removed through an outlet about 2 inches from the floor of the reactor and drawn past a back pressure gauge to a cold trap. To prevent condensation upstream from the back pressure gauge, steam tracing maintained the offgas temperature above 100° C.

After passing through a cold trap at 0° C. to remove condensible by-products, the dried product gas was analyzed by gas chromatograph to determine selectivity. In addition, a paramagnetic oxygen analyzer was used to determine the concentration of unreacted oxygen. The total unreacted oxygen mass as determined by gas chromatograph and oxygen analyzer was generally within about 90% agreement.

Table 1 illustrates the data from 14 runs using the stainless steel reactor.

TABLE 1

| Ex. # | Press. (PSIA) | Temp. (C.) | C3 (PSIA) | O2 (Vol.) (%) | Resid. O2 (V %) | Resid. Time (Sec) | Selectivity PO (%) | Selectivity PO + DER (%) | Conver. C3 (%) | Conver. O2 (%) |
|---|---|---|---|---|---|---|---|---|---|---|
| 1 | 220 | 267 | 123 | 7.1 | 3.0 | 75 | 33.2 | 42.2 | 5.1 | 53 |
| 2 | 220 | 267 | 150 | 7.2 | 1.3 | 90 | 38.0 | 48.9 | 7.9 | 82 |
| 3 | 220 | 271 | 82 | 6.9 | 2.0 | 60 | 28.6 | 37.1 | 10.9 | 72 |
| 4 | 226 | 261 | 81 | 7.2 | 2.9 | 198 | 28.4 | 35.8 | 7.1 | 61 |
| 5 | 230 | 266 | 129 | 7.1 | 1.9 | 50 | 32.9 | 39.7 | 5.9 | 74 |
| 6 | 232 | 270 | 147 | 9.3 | 1.4 | 260 | 14.7 | 41.4 | 8.0 | 84 |
| 7 | 419 | 272 | 188 | 6.5 | 0.8 | 62 | 40.6 | 48.8 | 10.2 | 88 |
| 8 | 505 | 222 | 290 | 7.0 | 2.0 | 133 | 21.3 | 34.4 | 5.0 | 72 |
| 9 | 510 | 259 | 202 | 6.8 | 0.9 | 72 | 30.2 | 38.7 | 9.7 | 85 |
| 10 | 513 | 203 | 363 | 7.8 | 2.2 | 167 | 16.6 | 35.6 | 4.5 | 67 |
| 11 | 516 | 215 | 273 | 7.1 | 2.4 | 205 | 18.8 | 40.7 | 5.1 | 64 |
| 12 | 815 | 199 | 471 | 7.8 | 1.5 | 165 | 16.6 | 38.7 | 6.0 | 75 |
| 13 | 820 | 209 | 284 | 6.5 | 1.5 | 215 | 20.9 | 33.4 | 8.9 | 79 |
| 14 | 824 | 199 | 604 | 7.2 | 1.4 | 72 | 22.0 | 34.5 | 4.4 | 78 |

Figure 2:
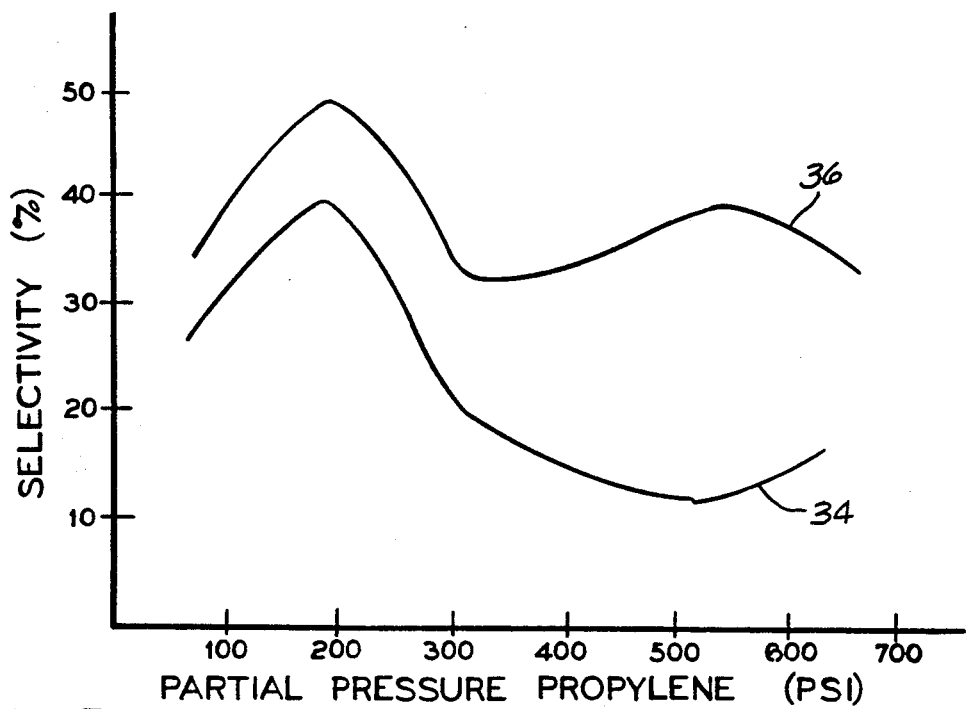
FIG. 2 shows in graphical representation the selectivity of propylene oxide and propylene oxide derivatives as a function of the partial pressure of propylene.

FIG. 2 is a graphical representation of the selectivity of propylene oxide as designated by reference numeral 34 and propylene oxide and its derivatives as designated by reference numeral 36. The data presented in FIGS. 2–4 was obtained from Table 1. An improved selectivity at about 200 psia is apparent.

Figure 3:
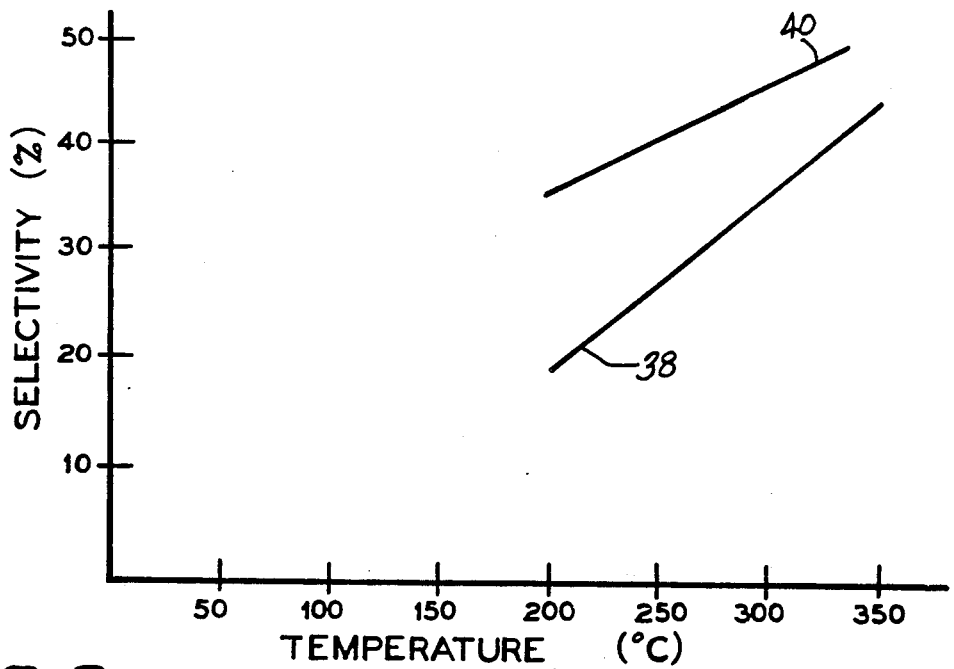
FIG. 3 shows in graphical representation the selectivity of propylene oxide and propylene oxide derivatives as a function of temperature.

FIG. 3 is a graphical representation of the effect of temperature on selectivity. Increasing the temperature improves the selectivity of both propylene oxide (as designated by reference numeral 38) and propylene oxide and its derivatives (as designated by reference numeral 40). Further increases in temperature will result in combustion and decreased yield.

Figure 4:
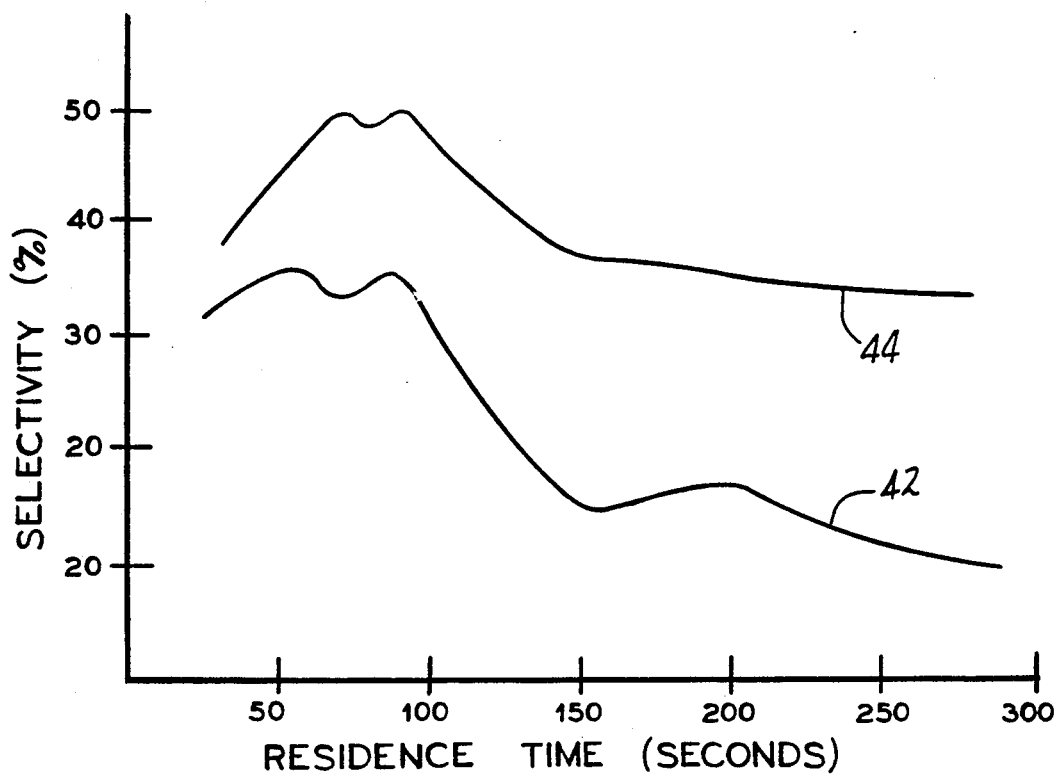
FIG. 4 shows in graphical representation the selectivity of propylene oxide and propylene oxide derivatives as a function of reaction time.

FIG. 4 is a graphical representation of percent selectivity of propylene oxide (reference numeral 42) and propylene oxide and its derivatives (reference numeral 44). The selectivity of both decreases when the residence time exceeds about 100 seconds.

Figure 5:
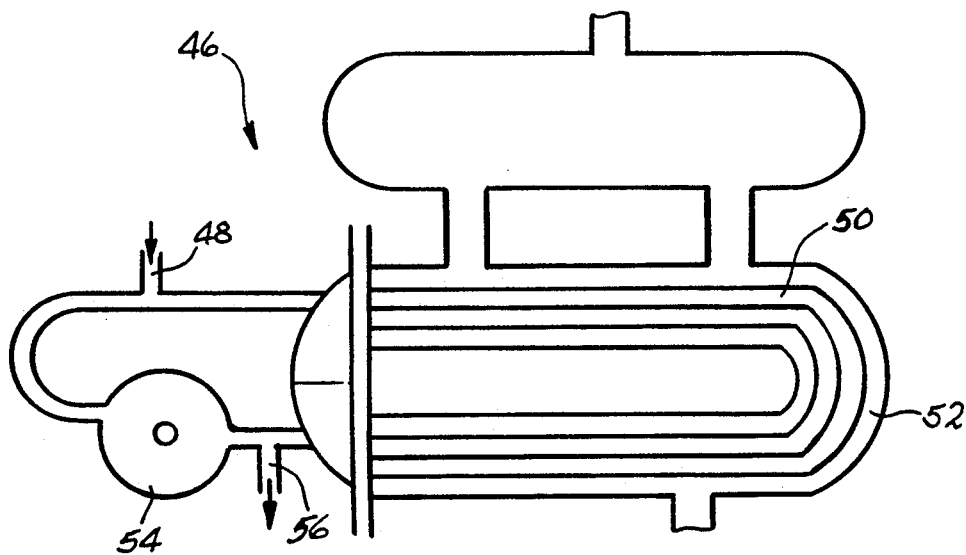
FIG. 5 shows in schematic a gas loop continuous stirred tank reactor used to circulate the mixture of gases in accordance with a second embodiment of the invention.

While the reaction has been described in terms of a continuous stirred tank reactor, any reactor capable of circulating reaction gases to achieve an isothermal reaction may be utilized. One alternative which it is believed will constitute a preferred embodiment is a gas phase loop reactor 46 as illustrated in schematic in FIG. 5 and described more fully in co-pending U.S. patent application Ser. No. 07/741,713 entitles Gas Phase Loop Reactor by Fullington, filed on even date hereof and incorporated in its entirety herein.

The gas phase loop reactor 46 recirculates gaseous reactants while providing a large surface area for the removal of heat. The reaction gases enter the reactor through inlet 48 and circulate through reaction loops 50. A water jacket 52 surrounds the reaction loops 50 to remove heat generated by the exothermic reaction.

A gas blower 54 continuously cycles the reaction gases through the reactor 46 with offgas being removed through outlet 56.

The patents and patent applications cited herein are intended to incorporated in their entireties.

It is to be understood that the above described embodiments of the invention are illustrative only and that modifications throughout may occur to those skilled in the art. Accordingly, this invention is not to be regarded as limited as defined by the appended claims.

We claim:

1. A process for the production of an alkylene oxide or mixture of alkylene oxides from a gaseous mixture comprising at least one hydrocarbon selected from the group consisting of alkylenes, alkanes and derivations thereof and oxygen, said process comprising:
    (a) circulating said mixture in a reactor vessel; and
    (b) oxidizing said hydrocarbon under substantially isothermal and essentially non-catalytic conditions while maintaining a hydrocarbon partial pressure of from about 80 to about 300 psia and a reaction temperature of from about 200° C. to about 350° C.

2. The process of claim 1 wherein said hydrocarbon is selected to be propylene, propane, or mixtures thereof and the residence time within said reactor vessel is less than about 150 seconds.

3. The process of claim 2 wherein a diluent selected from the group consisting of nitrogen, argon, acetaldehyde, methane, carbon dioxide and mixtures thereof is added to said reactor vessel.

4. The process of claim 3 wherein said diluent is either nitrogen or carbon dioxide.

5. The process of claim 4 wherein said hydrocarbon is propylene.

6. The process of claim 5 wherein sufficient oxygen is provided such that from about 0.5 vol. % to about 3.0 vol. % oxygen remains unreacted after completion of the residence time.

7. The process of claim 6 wherein the temperature gradient within said reactor vessel is less than about 5° C.

8. The process of claim 5 wherein from about 30 vol. % to about 85 vol. % propylene, from about 1 to about 20 vol. % oxygen and the balance carbon dioxide are circulated within said reaction vessel.

9. The process of claim 8 wherein from about 40 vol. % to about 75 vol. % propylene, from about 2 to about 17 vol. % oxygen and the balance carbon dioxide are circulated within said reaction vessel.

10. The process of claim 8 wherein from about 40 vol. % to about 75 vol. % propylene, from about 5 to about 15 vol. % oxygen and the balance carbon dioxide are circulated within said reaction vessel.

11. The process of claim 6 wherein said reaction temperature is from about 235° C. to about 300° C.

12. The process of claim 11 wherein said reaction temperature is from about 245° C. to about 290° C.

13. The process of claim 9 wherein said reaction temperature is from about 235° C. to about 300° C.

14. The process of claim 11 wherein the partial pressure of said propylene is from about 100 psia to about 250 psia.

15. The process of claim 14 wherein the partial pressure of said propylene is from about 120 psia to about 220 psia.

16. The process of claim 13 wherein the partial pressure of said propylene is from about 100 psia to about 250 psia.

17. The process of claim 16 wherein the partial pressure of said propylene is from about 120 psia to about 220 psia.

18. The process of claim 14 wherein said residence time is from about 5 seconds to about 125 seconds.

19. The process of claim 18 wherein said residence time is from about 10 seconds to about 100 seconds.

20. The process of claim 16 wherein said residence time is from about 5 seconds to about 125 seconds.

21. The process of claim 20 wherein said residence time is from about 10 seconds to about 100 seconds.

22. The process of claim 18 wherein said reactor vessel is a continuous stirred tank reactor.

23. The process of claim 18 wherein said reactor vessel is a gas phase loop reactor.

24. The process of claim 20 wherein said reactor vessel is a continuous stirred tank reactor.

25. The process of claim 20 wherein said reactor vessel is a gas phase loop reactor.

* * * * *